Figure 1:
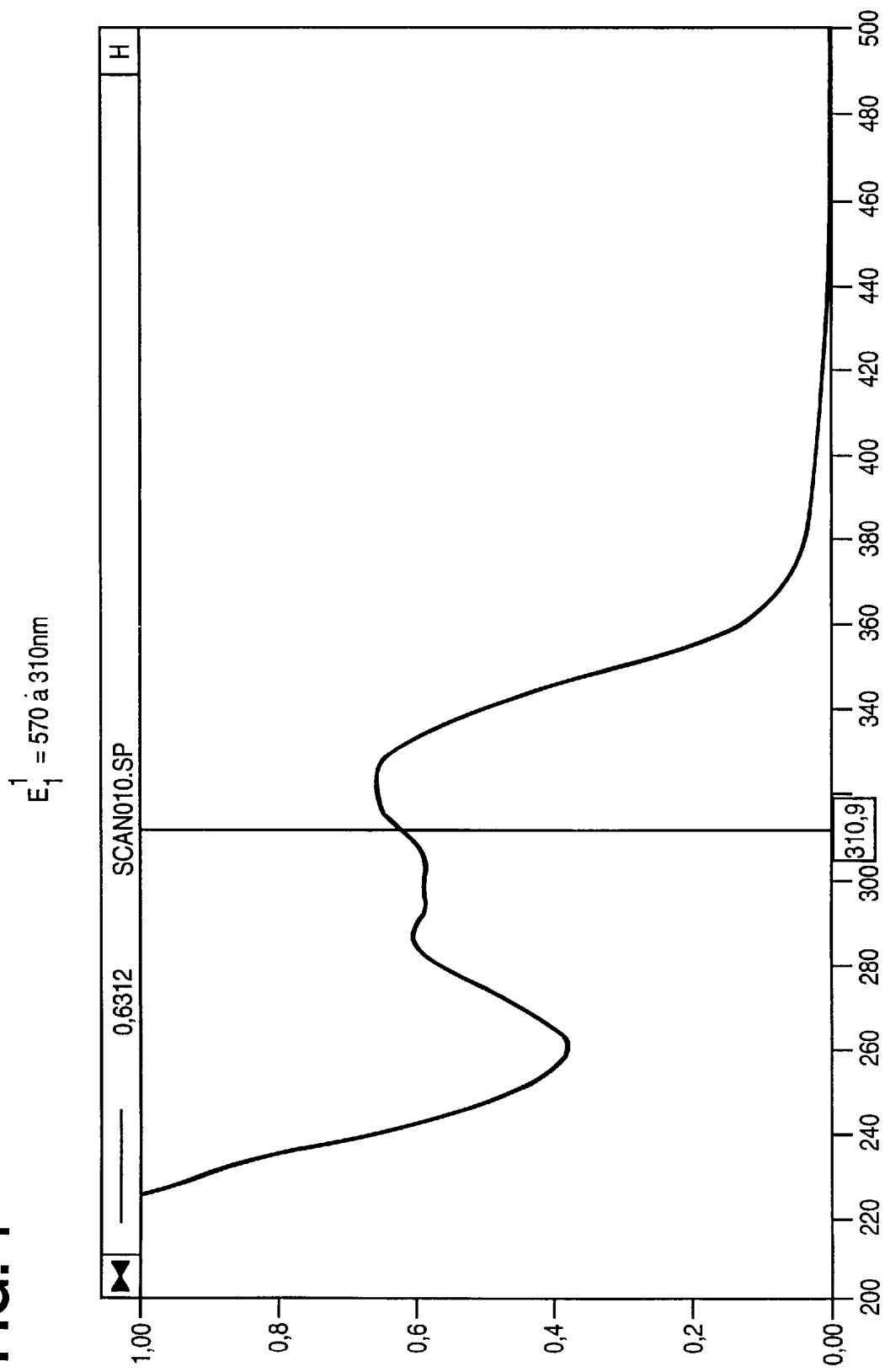

United States Patent
Tarroux et al.

[11] Patent Number: 5,869,031
[45] Date of Patent: Feb. 9, 1999

[54] DEPIGMENTING DERMATOLOGICAL AND/OR COSMETIC COMPOSITION

[75] Inventors: Marie-Christine Tarroux, Toulouse; Roger Navarro, Pamiers; Philippe Msika, Toulouse; Bernard Fabre, Belberaud, all of France

[73] Assignee: Pierre Fabre Dermo-Cosmetique, France

[21] Appl. No.: 913,742
[22] PCT Filed: Mar. 21, 1996
[86] PCT No.: PCT/FR96/00422
  § 371 Date: Sep. 23, 1997
  § 102(e) Date: Sep. 23, 1997
[87] PCT Pub. No.: WO96/29050
  PCT Pub. Date: Sep. 26, 1996

[30] Foreign Application Priority Data
Mar. 23, 1995 [FR] France .................. 95 03425

[51] Int. Cl.⁶ .................. A61K 7/42; A61K 7/48
[52] U.S. Cl. .................. 424/62; 424/59; 424/195.1
[58] Field of Search .................. 424/62, 59, 195.1

[56] References Cited

U.S. PATENT DOCUMENTS

| | | | |
|---|---|---|---|
| 5,085,870 | 2/1992 | Seguin et al. | 424/547 |
| 5,559,146 | 9/1996 | Sablon | 514/648 |
| 5,607,692 | 3/1997 | Ribier et al. | 424/450 |

FOREIGN PATENT DOCUMENTS

| | | |
|---|---|---|
| 0 307 277 | 3/1989 | European Pat. Off. . |
| 2.150.206 | 6/1973 | France . |

*Primary Examiner*—Sally Gardner-Lane
*Attorney, Agent, or Firm*—Rockey, Milnamow & Katz, Ltd.

[57] ABSTRACT

A dermatological and/or cosmetic composition containing a depigmenting active extract of mouse-ear hawkweed and the use thereof in a cosmetic treatment method are disclosed. The use of an active substance obtainable from mouse-ear hawkweed for preparing a depigmenting active medicament is also disclosed.

9 Claims, 1 Drawing Sheet

DEPIGMENTING DERMATOLOGICAL AND/OR COSMETIC COMPOSITION

This application claims priority under 35 USC 371 based upon PCT/FR96/00422 filed Mar. 21, 1996 and under 35 USC 119 based upon FR 95 03425 filed Mar. 23, 1995.

The present invention relates to novel dermocosmetic compositions which have depigmenting activity.

The color of the skin is due to several substances: haemoglobin in the blood vessels, carotenoids in the dermis and, especially, melanin in the epidermis.

This melanin is produced by melanocytes in the basal layer, under the action of tyrosinase, copper and oxygen.

Under the effect of exogenous or endogenous stimulations, changes in skin color may appear. These are dyschromias.

A change in the skin pigmentation may take place:

either by excess: hyperchromia, or by deficit: hypochromia.

This may take place in the epidermis or in the dermis and may be due to a variation in the amount of melanin or in the number of melanocytes.

Hyperchromias are accumulations of melanin pigments, carotenoids or exogenous pigments.

The melanin in the skin is formed by a complex association of eumelanin and pheomelanin.

Their biosyntheses are common up to dopaquinone (double oxidation of tyrosine by tyrosinase, a cuproproteinic enzyme). Their synthetic routes then diverge.

Brown eumelanin is an indole-5,6-quinone polymer, whereas pheomelanin, which is responsible for the red color, is a compound containing close to 10% sulfur and has a structure which is a polymer of cysteinyldopa.

Enzymes other than tyrosinase participate in the creation and control of melanins:

dopachrome oxidoreductase: which converts dopachrome into 5,6-dihydroxyindole and controls melanogenesis in the absence of tyrosinase, α-glutamyl transpepsidase converts glutathionedopa into cysteinyldopa, the glutathione system (reductase-peroxidase) which controls the crossroad between the biosynthesis of eumelanin and pheomelanin.

It appears that the surrounding sulfur level is the determining factor of such an orientation.

The glutathione reductase activity and the level of reduced glutathione are higher in people with ginger pigmentation than in those with brown pigmentation.

Dopachrome tautomerase regulates the reaction of dopachrome 5,6-dihydroxyindole-2-carboxylic acid and controls the proportion of carboxylated subunits in the melanin polymer.

Agents which depigment or whiten the complexion are chemical compounds that are capable of acting at the tissue, cellular or subcellular level.

They act on melanin itself or on the existence of melanocytes (melanocytotoxicity).

The general modes of action may be as follows:

inhibition of the formation of melanosomes, adverse change in the structure of melanosomes, inhibition of tyrosinase biosynthesis, inhibition of melanin biosynthesis, interference of the transfer of melanosomes into the keratinocytes, chemical effect on melanin with an increase in the degradation of melanosomes in the keratinocytes.

Moreover, it is necessary to demonstrate and eliminate the factor which induces hyperpigmentation before treating it (U.V., perfume, oestroprogestative, and to recommend a maximum-type sun protection throughout the medical treatment).

The motivations which compel people to bleach their skin may be very diverse.

Direct lightening of the skin is desired in Black Africa, with traditional or chemical solutions which have considerable harmful side effects on the appearance and structure of the skin.

The pallor or whiteness of asiatic facial skin is obtained with molecules which act with the least possible toxicity (arbutin, kojic acid and ascorbic acid).

The treatment of hyperpigmentation marks in white people requires the use of diverse molecules, the main one of which, hydroquinone, is the subject of intense scrutiny and its maximum cosmetic dose is 2%.

There is thus a need for compositions which have pronounced depigmenting activity at moderate concentrations, and which are well tolerated by the skin.

Accordingly, the subject of the present invention is a dermatological and/or cosmetic composition, characterized in that it contains a depigmenting active extract obtained from mouse-ear hawkweed.

Mouse-ear hawkweed, Hieracium pilosella, belongs to the family of Compositae. It is a small herbaceous ground-covering plant 10 to 30 cm in height.

The leaves form a basal rosette, they are long, oval and whitish underneath and covered with a silky down on both sides.

The flower-bearing stem is upright, single and bears a capitulum with hermaphroditic flowers, all ligulated, pentadentate and pale yellow in color. There are many bracts, often carrying black glandular hairs.

The fruit is a finely ribbed achene with aigrettes.

Mouse-ear hawkweed flowers from May to September.

It is found in dry locations, throughout almost all of Europe, in North Africa and in North America. It is very common in France but rare in the Mediterranean region.

Many chemical studies carried out on this plant have allowed a large number of molecules to be isolated and identified. Mouse-ear hawkweed is characterized by the presence of oxicoumarins: umbelliferone (7-hydroxycoumarin) and umbelliferone-7-monoglucoside or skimmine. The umbelliferone content varies according to the organs, with the leaves being the richest, and according to the seasons; the content is maximum in summer and minimum at the end of winter.

Phenolic acids have also been identified, as well as flavonoids: apigenin and its derivatives, luteolin and its derivatives. Certain authors note the presence of tannins throughout the plant.

Mouse-ear hawkweed has been used for its diuretic properties in traditional medicine. Its choleretic and cholagogic properties have also been described: thus, FR 2,549,373 uses essence of mouse-ear hawkweed for the preparation of a composition which aids digestion and bile secretion. Patent FR 744 M has proposed it as a hypocholesterolemiant. Aqueous compositions containing silanol and extracts of mouse-ear hawkweed have been proposed in FR 2,620,029 for the surface treatment of lymphatic vessels.

The Applicant has now revealed, unexpectedly, that active principles which can be prepared from mouse-ear hawkweed have properties that can advantageously be exploited in dermocosmetic compositions; the Applicant has revealed the depigmenting activity of an extract of mouse-ear hawkweed.

An active extract may be obtained in particular by a process which comprises a step of extraction from the aerial parts and/or roots of mouse-ear hawkweed, by a polar solvent chosen from the group comprising water, alcohol, acetone and mixtures thereof; in these aqueous-alcoholic and/or aqueous-acetone solvents, the proportion of each of the constituents may range between 0 and 100.

According to one of the embodiments of the invention, the plant is ground and then extracted with a $C_1$ to $C_4$ alcohol or with a water/$C_1$ to $C_4$ alcohol mixture or with acetone or with a water/acetone mixture, in water/$C_1$ to $C_4$ alcohol or water/acetone proportions ranging from 100/0 to 0/100. The plant/solvent ratio ranges from 1/5 to 1/20.

Preferably, the entire plant is ground and then extracted with a $C_1$ to $C_4$ alcohol or with a water/$C_1$ to $C_4$ alcohol mixture, in proportions ranging from 90/10 to 10/90.

The extraction may be carried out statically or with stirring, at temperatures ranging from the boiling point to room temperature. The duration of the extraction is between 1 hour and 24 hours. After extraction, the solutions are recovered by filtration or draining.

It is possible, in a second stage, to carry out steps of enriching in active principles.

The alcohols or the acetone are then evaporated off under vacuum, at temperatures between 40° C. and 100° C. The concentrated aqueous solutions are purified by liquid/liquid extraction.

The organic solvents used are alkane-type solvents, such as hexane or heptane, chlorinated solvents such as dichloromethane and chloroform, butanol, ethyl acetate or solvents whose miscibility with water depends on the ionic strength, such as acetone, isopropanol and ethanol. In this case, the aqueous solution will be saturated with $(NH_4)_2SO_4$, NaCl or $Na_2SO_4$. The pH of the liquid/liquid extraction may be adjusted to between pH 2.5 and pH 8 depending on the extraction solvents.

The organic phases are recovered and filtered.

The extract may be used in the present state. The organic solvent may also be evaporated off under vacuum, at a temperature between 40° C. and the boiling point of the solvent. The dry extract recovered is then ground in the form of a powder.

The various mouse-ear hawkweed extracts are assayed for their umbelliferone content, by high performance liquid chromatography. The assay is carried out on a $C_{18}$ column with a mobile phase: 95/5/15/0.5 water/propanol/tetrahydrofuran/phosphoric acid relative to a pure control sample of umbelliferone.

The contents vary according to the degree of purification of the extract. Thus, the proportions of umbelliferone relative to the solids content of an unpurified extract range from 0.5 to 2%, and for a purified extract from 4 to 10%.

The invention also comprises the use of a product with a composition similar to the mouse-ear hawkweed extract, but which may be prepared by synthesis.

Preferably, the mouse-ear hawkweed extract is present with an umbelliferone titer of between 0.05% and 10% by weight of the total composition.

The compositions according to the invention may be in the form of lotions, emulsions, creams, ointments, salves, etc. They also contain any formulation excipient known to those skilled in the art which is suitable for good topical application. They especially contain stabilizers, preserving agents, surfactants, fragrances and dyes.

In the compositions according to the invention, the active extract of mouse-ear hawkweed may be combined with keratolytic compounds, for example salicylic acid, lactic acid, glycolic acid or malic acid, as well as with other α-hydroxy acids known to those skilled in the art.

According to another aspect of the invention, the dermocosmetic compositions described above also contain a screening agent or a sunscreen; such inorganic and/or organic screening agents are known to those skilled in the art, who will adapt their choice and concentrations depending on the degree of protection desired.

The subject of the invention is also a cosmetic treatment method, characterized in that an extract of mouse-ear hawkweed is applied locally.

More particularly, the subject of the invention is the use, in a cosmetic treatment method, of an active extract of mouse-ear hawkweed in order to reduce and/or eliminate pigmentation marks.

Pigmentations often appear under the effects of UVA and B radiation, during prolonged exposure to sunlight.

The Applicant has thus evaluated the UV-screening and free-radical-trapping activities of extracts of mouse-ear hawkweed. These activities contribute towards the depigmenting activity of the extracts of mouse-ear hawkweed.

One of the aspects of the invention thus concerns the use, in a cosmetic method, of an extract of mouse-ear hawkweed as an anti-UVA and anti-UVB screening agent. It also relates to the use of an extract of mouse-ear hawkweed as an anti-radical substance.

The depigmenting properties of extracts of mouse-ear hawkweed or of an active product which may be prepared from mouse-ear hawkweed may, according to another aspect of the invention, lead to the use of an active product which can be obtained from mouse-ear hawkweed for the preparation of a medicinal product that is active as a depigmenting agent.

The pharmaceutical compositions will contain the extract of mouse-ear hawkweed combined with pharmaceutically acceptable excipients.

The examples which follow are intended to illustrate the invention without in any way limiting the scope thereof.

Reference will be made to FIG. 1 which represents the UV activity of an extract of mouse-ear hawkweed.

EXAMPLE 1

100 kg of whole mouse-ear hawkweed plants are ground and then extracted with 800 kg of 20% ethanol with stirring at reflux for 1 hour. The aqueous-alcoholic solution is recovered by draining and then filtered. It is then concentrated under vacuum at 60° C. until 100 kg of aqueous solution are obtained.

The pH of this solution is brought to pH 3.5 by addition of hydrochloric acid.

A liquid/liquid extraction is carried out with 300 kg of ethyl acetate with stirring for 2 hours. After separation of the phases by settling, the organic phase is recovered, concentrated under vacuum at 40° C. and then dried and ground. 1 kg of dry extract is recovered, the umbelliferone content of which is between 6 and 8%.

EXAMPLE 2

1 kg of whole mouse-ear hawkweed plants is extracted with 5 kg of cold 60% ethanol, for 24 hours. The aqueous-alcoholic solution is recovered by filtration. Its umbelliferone content is between 1 and 2% relative to the solids content.

EXAMPLE 3

10 kg of whole mouse-ear hawkweed plants are ground using a hammer mill. The plant meal is then extracted at reflux, with stirring, with 100 kg of a 50/50 methanol/water mixture. The solution is recovered by draining and then filtered. It is then concentrated under vacuum at 50° C. until 10 kg of aqueous concentrate are obtained. Ammonium sulfate is added to this concentrate to saturation, followed by 30 kg of isopropanol.

The mixture is stirred for 2 hours and is then left to separate by settling. The isopropyl phase is recovered, concentrated and then dried under vacuum.

4.5 kg of a powder are obtained, the umbelliferone content of which ranges from 4 to 6%.

EXAMPLE 4

1 kg of whole mouse-ear hawkweed plants is ground and then extracted with an 80/20 water/acetone mixture at reflux for one hour.

The aqueous-acetone solution obtained after filtration is concentrated and then dried under reduced pressure at a temperature between 40° and 50° C. The dry extract obtained is ground and then titrated to between 5 and 8% umbelliferone.

EXAMPLE 5
Evaluation of the sunscreen activity

The UVA and UVB sunscreen activity of the extract of mouse-ear hawkweed is evaluated by spectrophotometric study of the extract titrated to 5% umbelliferone.

This extract has an absorption maximum at 325 nm and a specific extension coefficient of 570 at 310 nm.

This demnonstrates the UVB screening potential of the extract of mouse-ear hawkweed. By comparison, Parsol MCX, a chemical UVB screening agent, has a specific extension coefficient of 810 at 310 nm.

The results are represented in the figure appended to the application.

EXAMPLE 6
Evaluation of the anti-radical activity

Radical reactions are divided into 3 successive steps: initiation, propagation and disappearance of the free radicals:

initiation is due to the superoxide anion $O_2^-$ which appears under the effect of factors such as UV radiation or stress, propagation is brought about by the hydroxyl radicals OH, disappearance of the free radicals. Free radical traps act on the superoxide anion $O_2^-$ but also on the hydroxyl radicals. Thus, we have sought to evaluate the anti-radical activity on these two steps.

The activity on the superoxide anion is carried out by testing in vitro. The superoxide anion is generated by radical photo-oxidation, by sensitization of riboflavin with visible radiation.

The colored indicator used is tetrazolium nitro blue, an electrophile, which is reduced by the superoxide anion generated to diformazan.

The anti-radical activity of the extract of mouse-ear hawkweed is expressed by the concentration of extract which inhibits 50% of the reductive activity of the superoxide anion on TNB, the $IC_{50}$. For an extract of mouse-ear hawkweed titrated to 5% umbelliferone, the $IC_{50}$ is 0.3 mg/ml.

The activity on radical propagation, and thus on the hydroxyl radicals, is evaluated on DPHH, diphenyl-picrylhydrazyl hydrate, which is a stable, colored free radical. The $IC_{50}$ of an extract of mouse-ear hawkweed containing 5% umbelliferone is 0.025 mg/ml. In this test, vitamin E has an $IC_{50}$ of 0.006 mg/ml.

EXAMPLE 7
Evaluation of the depigmenting activity in vitro

In vitro, an inhibitory activity on the activity of tyrosinase, the main enzyme involved in the pigmentation process, is desired. In the presence of oxygen, the reaction of tyrosinase with tyrosine is reflected by an increase in the optical density of the reaction medium at 280 nm.

Any inhibition of the action of tyrosinase on tyrosine, directly on the enzyme or indirectly by competition with tyrosine, results in a smaller increase in the optical density at 280 nm.

The $IC_{50}$, the concentration of extract of mouse-ear hawkweed which inhibits the tyrosinase reaction signal by 50%, is calculated.

For an extract of mouse-ear hawkweed assayed at 5% umbelliferone, the $IC_{50}$ is 30 µg/ml.

EXAMPLE 8
Depigmentation in vivo

Evaluation of the depigmenting activity consists in searching for an inhibitory effect of topical preparations containing an extract of mouse-ear hawkweed titrated to 5% umbelliferone on the hyperpigmentation of the caudal epidermis, induced by exposure of pigmented mice to ultraviolet radiation.

The topical preparation is applied 7 days a week for 6 consecutive weeks, with UV irradiation 5 days a week for 42 days.

The animals are subjected to a daily examination in order to monitor the changes in pigmentation and to evaluate their intensity. The colorations are assigned values according to a color scale.

The animals treated with the extract of mouse-ear hawkweed exhibit non-uniform depigmentation when compared with the irradiated control batch. This effect cannot be attributed to a UV screening effect since the products are applied after the irradiation.

After the 42 days of treatment, the skin of the caudal appendix of the animals is removed after they have been sacrificed. The optical density at 700 nm is measured on the sample of epidermis.

A significant decrease in the optical density of the epidermis of the animals treated with extract of mouse-ear hawkweed is observed. This decrease reflects the depigmenting effect of this extract.

Lastly, the distribution and quantification of melanin in the layers of the epidermis are evaluated by image analysis.

A 24% overall decrease in melanin is observed, which is found both in the basal and in the surface layers of the epidermis of mice treated with the extract of mouse-ear hawkweed.

EXAMPLE 9
Depigmenting formulae

The following formulae may be given by way of example:

| A - Depigmenting lotion | |
|---|---|
| Extract of mouse-ear hawkweed with a 4% titer | 10 g |
| Propylene glycol | 20 g |
| Ethyl alcohol | 10 g |
| Distilled water qs | 100 g |

The extract of mouse-ear hawkweed is dissolved in the propylene glycol/ethyl alcohol mixture and then completed with distilled water.

| B - Aqueous gel | |
|---|---|
| Extract of mouse-ear hawkweed with an 8% titer | 5 g |
| Propylene glycol | 20 g |
| Ethyl alcohol | 15 g |
| Hydroxypropylcellulose | 1.5 g |
| Distilled water qs | 100 g |

The extract of mouse-ear hawkweed is dissolved in the propylene glycol/ethyl alcohol mixture and then completed with distilled water.

The cellulose is introduced with stirring until the gel forms.

| C - Emulsion | |
|---|---|
| Extract of mouse-ear hawkweed with a 4% titer | 3 g |
| Glucose ester (Glucate SS) | 4 g |
| Ethoxylated glucose ester (Glucate SSE 20) | 4 g |
| Thick liquid petroleum jelly | 10 g |
| $C_8$–$C_{10}$ triglycerides | 4 g |
| Cyclomethicone (Dow Corning 345) | 4 g |
| Carboxyvinyl polymer (Carbomer 940) | 1 g |
| EDTA, 2 Na | 0.2 g |
| Distilled water qs | 100 g |

EXAMPLE 10
Roll-on containing depigmenting fluid

| | |
|---|---|
| Extract of mouse-ear hawkweed | 0.1 to 10% |
| 95° alcohol | 35 to 75% |
| Isopropyl adipate | 5 to 15% |
| Oleic acid | 0.01 to 1% |
| Propylene glycol | 10 to 40% |
| Klucel MF | 0.1 to 2% |
| Water qs | 100 |

EXAMPLE 11
Depigmenting/anti-radical/keratolytic fluid

| | |
|---|---|
| Extract of mouse-ear hawkweed | 0.1 to 10% |
| Salicylic acid | 0.1 to 5% |
| Vitamin C PCA | 0.1 to 10% |
| Hydroquinone | 0.1 to 5% |
| Batyl alcohol | 0.05 to 1% |
| 95° alcohol | 10 to 75% |
| Isopropyl adipate | 5 to 15% |
| Oleic acid | 0.01 to 1% |
| Propylene glycol | 5 to 40% |
| Klucel MF | 0.1 to 2% |
| Water qs | 100 |

EXAMPLE 12
Depigmenting day cream

| | |
|---|---|
| Arlacel 165 (ICI) | 5 to 15% |
| Cetyl alcohol | 0.1 to 3% |
| Stearic acid | 1 to 6% |
| Liquid paraffin | 2 to 15% |
| Isopropyl isostearate | 1 to 6% |
| Sunflower oil | 1 to 2% |
| Extract of mouse-ear hawkweed | 0.1 to 25% |
| Batyl alcohol | 0.05 to 1% |
| AHA | 0.1 to 25% |
| Propylene glycol | 0.1 to 10% |
| Water qs | 100 |

EXAMPLE 13
O/W depigmenting roll-on

| | |
|---|---|
| Arlamol E | 0.1 to 10% |
| Brij 72 | 1 to 3% |
| Brij 721 | 1 to 5% |
| Extract of mouse-ear hawkweed | 0.1 to 25% |
| Oleic acid | 0.05 to 1% |
| Water qs | 100 |
| Alcohol | 0 to 10% |

EXAMPLE 14
O/W depigmenting milk

| | |
|---|---|
| Arlatone 985 | 1 to 5% |
| Brij 721 | 1 to 3% |
| Miglyol 812 | 1 to 10% |
| Arlamol MD | 1 to 10% |
| Extract of mouse-ear hawkweed | 0.1 to 25% |
| Atlas G 2330 | 0.1 to 5% |
| Salicylic acid | 0.1 to 2% |
| Alcohol | 0 to 10% |
| α-Bisabolol | 0.05 to 0.5% |
| Magnesium vitamin C phosphate | 0.1 to 3% |
| Water qs | 100 |

EXAMPLE 15
Moisturizing and depigmenting emulsion protective against UVB and A

| | |
|---|---|
| Extract of mouse-ear hawkweed | 0.1 to 25% |
| Arlacel 2121 | 1 to 10% |
| Arlamol HD | 1 to 10% |
| Alcohol | 0 to 10% |
| Oleic acid | 0.1 to 1% |
| Behenyl alcohol | 0.1 to 2% |
| Tocopheryl acetate | 0.05 to 1% |
| Glycerol | 0.01 to 10% |
| AHA | 0.1 to 25% |
| Vitamin C PCA | 0.1 to 3% |
| Glycerol | 0.1 to 15% |
| $TIO_2$ | 0 to 25% |
| ZnO | 0 to 25% |
| Cinnamate | 0 to 10% |
| Dibenzoylmethane | 0 to 4% |
| Water qs | 100 |

EXAMPLE 16
Depigmenting W/O emulsion night cream

| | |
|---|---|
| Arlacel 481 | 2 to 10% |
| Paraffin | 1 to 20% |
| Glycerol | 1 to 15% |
| $MgSO_4$ | 0.5 |
| Water qs | 100 |
| Extract of mouse-ear hawkweed | 0.1 to 25% |

EXAMPLE 17
Nourishing depigmenting emulsion

| | |
|---|---|
| Arlacel 1689 | 1 to 5% |
| Miglyol 812 | 1 to 15% |
| Aerosil 972 | 0.1 to 0.5% |
| Glycerol | 1 to 15% |
| MgSO$_4$ | 0.1 to 0.5% |
| Water qs | 100 |
| Extract of mouse-ear hawkweed | 0.1 to 25% |
| Batyl alcohol | 0.05 to 0.3% |

EXAMPLE 18
Depigmenting stick

| | |
|---|---|
| Super Hartolan | 9% |
| Lunacera Alba | 4.5% |
| Lunacera C 40 | 7.2% |
| Lunacera C 46 | 3.7% |
| Lunacera M | 4.5% |
| Petroleum jelly | 0 to 18% |
| Castor oil | 0 to 28% |
| Isopropyl myristate | 0 to 30% |
| TiO$_2$ - Mica (Timica Silk blue) | 0.1 to 5% |
| Ultra-fine TiO$_2$ | 0 to 25% |
| Ultra-fine ZnO | 0 to 25% |
| Extract of mouse-ear hawkweed | 0.1 to 25% |
| Batyl alcohol | 0.05 to 1% |
| β-Carotene | 0.005 to 0.1% |
| Abil WE 09 | 0.1 to 2% |
| Water qs | 0 to 5% |

EXAMPLE 19
Depigmenting ultra-fine spray-emulsion

| | |
|---|---|
| Ethoxylated behenyl alcohol (Mergital B 10) | 5 to 10% |
| Vegetable oil | 0.1 to 5% |
| Lanette 22 | 0.1 to 2% |
| Extract of mouse-ear hawkweed | 0.1 to 25% |
| Vitamin C palmitate | 0.1 to 3% |
| AHA | 0.1 to 25% |
| α-Bisabolol | 0.05 to 0.5% |
| Water qs | 100 |

We claim:

1. A method for reducing or eliminating excessive pigmentation marks comprising locally administering to a subject in need of such treatment an effective amount of an extract of mouse-ear hawkweed.

2. A method according to claim 1, characterized in that the extract is obtained after a step of extraction by a solvent chosen from the group consisting of water, alcohol, acetone and mixtures thereof in all proportions, from the aerial parts and/or the roots of mouse-ear hawkweed.

3. A method according to claim 2, characterized in that the extract is obtained after a step of aqueous-alcoholic extraction, with a water/alcohol ratio of between 90/10 and 10/90, from the aerial parts and/or the roots of mouse-ear hawkweed.

4. A method according to claim 1, comprising coadministering at least one other depigmenting active principle.

5. A method according to claim 1, comprising coadministering at least one organic or inorganic sunscreen.

6. A method according to claim 1, comprising coadministering at least one keratolytic active principle.

7. A method according to claim 1, characterized in that the extract of mouse-ear hawkweed is present in an umbelliferone titer of between 0.05% and 10% of the total composition.

8. A method according to claim 1, in which the extract of mouse-ear hawkweed also acts as an anti-UVA and B screening agent.

9. A method according to claim 8, in which the extract of mouse-ear hawkweed also acts as an anti-radical substance.

* * * * *